United States Patent
Furrer et al.

(10) Patent No.: US 9,140,713 B2
(45) Date of Patent: Sep. 22, 2015

(54) METHOD FOR OPERATING AN AUTOMATED SAMPLE WORKCELL

(71) Applicant: Roche Diagnostics Operations, Inc., Indianapolis, IN (US)

(72) Inventors: Frederic Furrer, Horw (CH); Joerg Haechler, Oberwil b. Zug (CH); Andrzej Knafel, Walchwil (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/681,130

(22) Filed: Apr. 8, 2015

(65) Prior Publication Data

US 2015/0212104 A1    Jul. 30, 2015

Related U.S. Application Data

(62) Division of application No. 13/445,282, filed on Apr. 12, 2012, now Pat. No. 9,029,159.

(30) Foreign Application Priority Data

Apr. 29, 2011    (EP) .................................... 11164310

(51) Int. Cl.
*G01N 35/02* (2006.01)
*G01N 35/00* (2006.01)
(Continued)

(52) U.S. Cl.
CPC .... *G01N 35/00732* (2013.01); *G01N 35/00871* (2013.01); *G01N 35/04* (2013.01);
(Continued)

(58) Field of Classification Search
CPC ............... G01N 2035/0094; G01N 35/00732; G01N 35/0092; G01N 35/0095; G01N 2035/0493; G01N 15/1429; G01N 2035/00495; G01N 2035/00752; G01N 2035/00801; G01N 2035/0406; G01N 2035/0465; G01N 35/025; G01N 35/028; G01N 2035/0405; B01L 2300/021; B01L 2300/0627; B01L 3/5021; B01L 3/5082; B01L 9/06; B04B 13/00; B04B 2011/046

USPC .......... 422/50, 400, 401, 402, 403, 404, 405, 422/408, 62, 63, 64, 65, 67, 68.1, 73, 75, 422/82.05, 82.06, 82.07, 82.08, 82.09, 98, 422/500, 501, 504, 509, 5, 10, 511, 512, 422/514, 515, 521, 526, 547, 549, 550, 554, 422/556, 557, 558, 559, 560, 561, 562, 565, 422/566, 939, 940; 436/43, 46, 47, 164, 436/165, 169, 170, 815, 817; 435/13, 435/283.1, 287.1, 287.7, 287.8, 287.9, 435/288.7; 73/863.01, 864.21
See application file for complete search history.

(56) References Cited

U.S. PATENT DOCUMENTS

| | | | |
|---|---|---|---|
| 4,338,279 | A | 7/1982 | Orimo et al. |
| 5,865,718 | A | 2/1999 | Chan |

(Continued)

FOREIGN PATENT DOCUMENTS

WO    2007/018897 A3    2/2007

OTHER PUBLICATIONS

Felder, Robin A., "Automation of Preanalytical Processing and Mobile Robotics," Handbook of Clinical Automation, Robotics, and Optimization, edited by Gerald J. Kost, 1996, John Wiley & Sons, Inc., Chapter 12, pp. 252-282.

*Primary Examiner* — Dennis M White
(74) *Attorney, Agent, or Firm* — Roche Diagnostics Operations, Inc.

(57) ABSTRACT

A method of operating the automated sample workcell for processing one or more biological samples is presented. The method comprises receiving one or more biological samples. Each biological sample is contained in a sample tube. Each sample tube is a tube type. If a test order was received for at least one of the biological samples, the test order being indicative of one or more first processing steps, the workcell can automatically execute the one or more first processing steps. If the test order was not received, one or more second processing steps can be determined based on the tube type of the sample tube that contains the at least one biological sample and the one or more second processing steps can then be executed.

20 Claims, 5 Drawing Sheets

(51) Int. Cl.
*G01N 35/04* (2006.01)
*B04B 13/00* (2006.01)
*B04B 11/04* (2006.01)
*B01L 9/06* (2006.01)
*B01L 3/00* (2006.01)

(52) U.S. Cl.
CPC ............ *B01L 3/5021* (2013.01); *B01L 3/5082* (2013.01); *B01L 9/06* (2013.01); *B01L 2300/021* (2013.01); *B01L 2300/0627* (2013.01); *B04B 13/00* (2013.01); *B04B 2011/046* (2013.01); *G01N 35/025* (2013.01); *G01N 35/028* (2013.01); *G01N 2035/00495* (2013.01); *G01N 2035/00752* (2013.01); *G01N 2035/00851* (2013.01); *G01N 2035/0405* (2013.01); *G01N 2035/0406* (2013.01); *G01N 2035/0465* (2013.01); *G01N 2035/0493* (2013.01)

(56) References Cited

U.S. PATENT DOCUMENTS

| | | |
|---|---|---|
| 6,599,476 B1 | 7/2003 | Watson et al. |
| 2005/0037502 A1 | 2/2005 | Miller |
| 2005/0129576 A1 | 6/2005 | Oonuma |
| 2007/0020764 A1 | 1/2007 | Miller |
| 2010/0104478 A1 | 4/2010 | Kondou |
| 2010/0111767 A1 | 5/2010 | Yonekura et al. |

METHOD FOR OPERATING AN AUTOMATED SAMPLE WORKCELL

CROSS-REFERENCE TO RELATED APPLICATIONS

This application is a divisional of U.S. patent application Ser. No. 13/445,282 filed Apr. 12, 2012, now allowed, which is based on and claims priority to EP 11164310.2, filed Apr. 29, 2011, which is hereby incorporated by reference.

BACKGROUND

The present disclosure generally relates to an automated sample workcell and a method for operating an automated sample workcell and, in particular, to an automated sample workcell which is operable to process biological samples and a method for operating an automated sample workcell.

In analytical laboratories, in particular clinical laboratories, a multitude of analyses on biological samples are executed in order to determine the physiological state of a patient. Current pre-analytical specimen processors on the market are able to prepare a plurality of biological samples such as blood, urine, cerebral-spinal fluid, saliva, etc. Biological fluid samples are typically contained in open or capped sample tubes. Before a chemical or biological analysis can be performed on a biological sample, a plurality of different pre-analytical processing steps may have to be executed on a sample of a patient. Such processing steps may comprise centrifugation, capping, decapping, recapping and/or aliquotation steps. The processing steps may also comprise adding chemicals or buffers to a sample, concentrating a sample, incubating a sample, and the like. A growing number of those 'pre-analytical' steps and procedures are executed automatically by automated pre-analytical sample workcells, also known as 'automated pre-analytical systems'. The kind of analytical test to be executed on a biological sample is typically specified in a test order.

One typical problem is with the physical transport and processing of a sample may not always be synchronized with the assignment of a particular analytical test to the biological sample. For example, a blood sample may be drawn from a patient and collected in a sample tube which is then transported manually, or automatically, to an automated sample workcell at a moment in time when it may not clear which kind of biological and/or chemical analysis, also referred to as 'analytical test,' shall be executed on that sample. A physician may have to conduct additional examinations of the patient before he/she can decide which kind of analytical test should be executed on that blood sample of the patient. While the physician conducts the additional examinations, the blood sample of the patient may have already arrive at the automated sample workcell, leaving the automated sample workcell with the question what to do with the sample. According to some laboratory settings, a plurality of samples is received together with a pile of paper-based test orders. In those scenarios, the assignment of electronic test orders to samples may be delayed as the data on the paper-based test orders needs to be entered manually into the lab software before an electronic test order can be requested for a particular sample.

Most state-of-the-art automated sample workcells do not prepare a biological sample for a particular analysis as long as the test order for the sample has not received. Valuable time is lost, as the automated workcell is not able to process the biological sample at all or is merely able to carry samples not having assigned a test order to a buffering station.

Some state-of-the-art automated sample workcells do not request a test order but rather determine the type of the sample tubes of a biological sample and process the sample exclusively based on its tube type. For example, in one known system, the automated sample workcell determines the sample container type by image analysis for distributing the containers to different areas or racks. A disadvantage of this approach is that information on the tube type alone is often not sufficient to determine all processing steps necessary to prepare a particular biological sample for a particular analytical test. In addition, the systems are inflexible, because in a lab there may exist much more processing workflows and corresponding test orders than tube types.

Generally, state-of-the-art automated sample workcells are either completely test order based (and therefore completely dependent on the receipt of a test order) or are solely based on the determination of the tube type. In the latter case, the workcells are inflexible and often not able to sufficiently pre-process a biological sample for a particular analytical test.

Therefore, there is a need for an improved automated sample workcell which is operable to process one or more biological samples even in case no test order was received for the samples, thereby avoiding delays and speeding up sample processing

SUMMARY

In accordance with the present disclosure, an automated sample workcell and method of operating the automated sample workcell for processing one or more biological samples are disclosed. The automated sample workcell comprises a sample input station for receiving the at least one biological sample. Each biological sample is contained in a sample tube. Each sample tube is of a tube type. The automated sample workcell further comprises an instrument manager module for receiving a test order for the at least one received biological sample and a tube type detector for automatically determining the tube type of each of the at least one biological sample. If the test order was received, wherein the test order is indicative of one or more first processing steps, the automated sample workcell automatically executes the one or more first processing steps on the at least one biological sample. If the test order was not received, the automated sample workcell automatically determines one or more second processing steps based on the tube type of the sample tube that contains the at least one biological sample and executes the one or more second processing steps on the at least one biological sample.

Accordingly, it is a feature of the embodiments of the present disclosure to provide an improved automated sample workcell which is operable to process one or more biological samples even in case no test order was received for the samples, thereby avoiding delays and speeding up sample processing. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The expression 'automated sample workcell' as used herein can encompass any laboratory workcell comprising one or more lab-devices or 'workcell-units' which can automatically execute one or more processing steps on one or more biological samples. The expression 'processing steps' thereby can refer to physically executed processing steps such as centrifugation, aliquotation and the like. An 'automated sample workcell' can cover pre-analytical sample workcells, post-analytical sample workcells and also analytical workcells. In particular, an automated sample workcell can cover pre-analytical sample workcells. The lab-devices of an automated sample workcell can form a functional unit, i.e., they are controlled collectively for executing a sequence of processing steps on a sample. The lab-devices may, but do not necessarily have to, form a physical unit. Accordingly, the lab-devices of a work cell may form one monolithic block or may be a set of physically separated lab-devices which are connected by a transport unit (e.g. a conveyor).

A 'pre-analytical sample workcell' can comprise one or more lab-devices for executing one or more pre-analytical processing steps on one or more biological samples, thereby preparing the samples for one or more succeeding analytical tests. A pre-analytical processing step can be, for example, a centrifugation step, a capping-, decapping- or recapping step, an aliquotation step, a step of adding buffers to a sample and the like. The expression 'analytical system' as used herein can encompass any monolithic or multi-modular laboratory device comprising one or more lab-devices or operative units which are operable to execute an analytical test on one or more biological samples. The expression 'post-analytical sample workcell' as used herein can encompass any automated sample workcell being operable to automatically process and/or store one or more biological samples. Post-analytical processing steps may comprise a recapping step, a step for unloading a sample from an analytical system or a step for transporting the sample to a storage unit or to a unit for collecting biological waste.

The workcells may be connected by a transport unit (conveyor and/or robotic arm). Alternatively, samples can be transported from one workcell to the other manually or workcells are directly connected to each other.

The term 'biological sample' can encompass any kind of tissue or body fluid having been derived from a human or any other organism. In particular, a biological sample can be a whole blood-, serum-, plasma-, urine-, cerebral-spinal fluid-, or saliva-sample or any derivatives thereof.

An analyte can be a component of a sample to be analyzed, e.g. molecules of various sizes, ions, proteins, metabolites and the like. Information gathered on an analyte may be used to evaluate the impact of the administration of drugs on the organism or on particular tissues or to make a diagnosis. The determination of analytes and their concentrations within a biological sample is herein also referred to as 'clinical chemistry'. The characterization of the cellular components of blood samples is called 'clinical hematology'. Laboratory analyses for evaluating an individual's clotting mechanism are referred to as 'coagulation analyses'.

An Analysis or 'analytical test' can be a laboratory procedure characterizing a parameter of a biological sample, e.g. its opacity, color, or density or the presence or concentration of an analyte of the sample. Routine analyses are done on plasma or serum samples instead on whole blood samples because the cellular components of the blood interfere with some analytical tests. In addition, serum and plasma can be frozen or cooled and can therefore be stored for several days or weeks for subsequent analysis. Therefore, whole blood samples are commonly centrifuged in pre-analytical sample workcells in order to obtain plasma or serum samples before the samples are stored or analyzed.

A 'test order' as used herein can encompass any data object being indicative of one or more analytical tests to be executed on a particular biological sample. For example, a test order may be a file or an entry in a relational database. A test order can indicate an analytical test if, for example, the test order comprises or is stored in association with an identifier of an analytical test to be executed on a particular sample.

The term 'sample tube' can refer to any individual container for transporting, storing and/or processing a biological sample. In particular, the term without limitation can refer to a piece of laboratory glass- or plastic-ware optionally comprising a cap on its upper end and usually having a rounded U-shaped bottom. Sample tubes, e.g. sample tubes used to collect blood, often comprise additional substances such as clot activators or anticoagulant substances which have an impact on the processing of the sample. As a consequence, different tube types typically can be adapted for pre-analytical and analytical requirements of a particular analysis, e.g. a clinical chemistry analysis, a hematological analysis or a coagulation analysis. A mix up of sample tube types can make (blood) samples unusable for analysis. To prevent errors in the collection and handling of samples, the sample caps of many tube manufacturers are encoded according to a fixed and uniform color scheme. Some sample tubes types in addition or alternatively are characterized by particular tube dimensions, cap dimensions, and/or tube color. A dimension of a tube comprises e.g. its height, its size and/or further characteristic shape properties.

The expression 'tube type' can refer to a category of sample tubes which can be characterized by at least one shared property, whereby the shared property can be automatically detected by a lab-device and can thus be used to discriminate a set of sample tubes of a first tube type from another. Some examples for typical tube types currently in use are given in Table 1. Table 1 lists a set of sample tube types I-VII. Some tube types are designed for carrying biological samples which can be used for a plurality of different analytical tests. An example for such a tube type is a serum tube. However, a tube type may also be particular for one single analytical test.

Blood plasma is the liquid component of blood lacking the blood cells. Blood plasma is prepared by spinning whole blood samples containing anti-coagulant substances in a centrifuge until the blood plasma is separated from the blood cells at the bottom of the tube. A plasma sample is a blood sample from which plasma is to be prepared. Serum samples are commonly used for a clinical chemistry or immunology analysis. Blood serum is blood plasma without fibrinogen or the other clotting factors. Blood serum is commonly used for a broad variety of analyses such as analyses for the detection of antibodies, for clinical chemistry analyses, for blood typing, or for DNA analytics in a forensic laboratory. Correspondingly, a serum sample is a blood sample from which serum is to be prepared prior to executing one of the analyses. A coagulation sample tube is a sample tube for collecting blood to be used in a coagulation test.

A 'STAT sample' is a biological sample which needs to be processed and analyzed very urgently as the analysis result may be of life-crucial importance for a patient.

The expressions 'sorting' and 'grouping' will in the following be used synonymously in order to refer to the grouping of biological samples based on features shared by all samples of a particular group for processing all samples of a group in the same manner at least during a subsequent processing step.

According to embodiments, the evaluation if the test order was received can be executed upon receipt of the one or more samples. The receipt of the one or more samples can, for example, initiate the execution of a first request for a test order of the sample. These features can be advantageous because they can allow the execution of at least some processing steps on the at least one biological sample even if no test order was received. As a consequence, delays can be avoided and the sample processing workflow can be executed by the workcell more efficiently.

Figure 1:
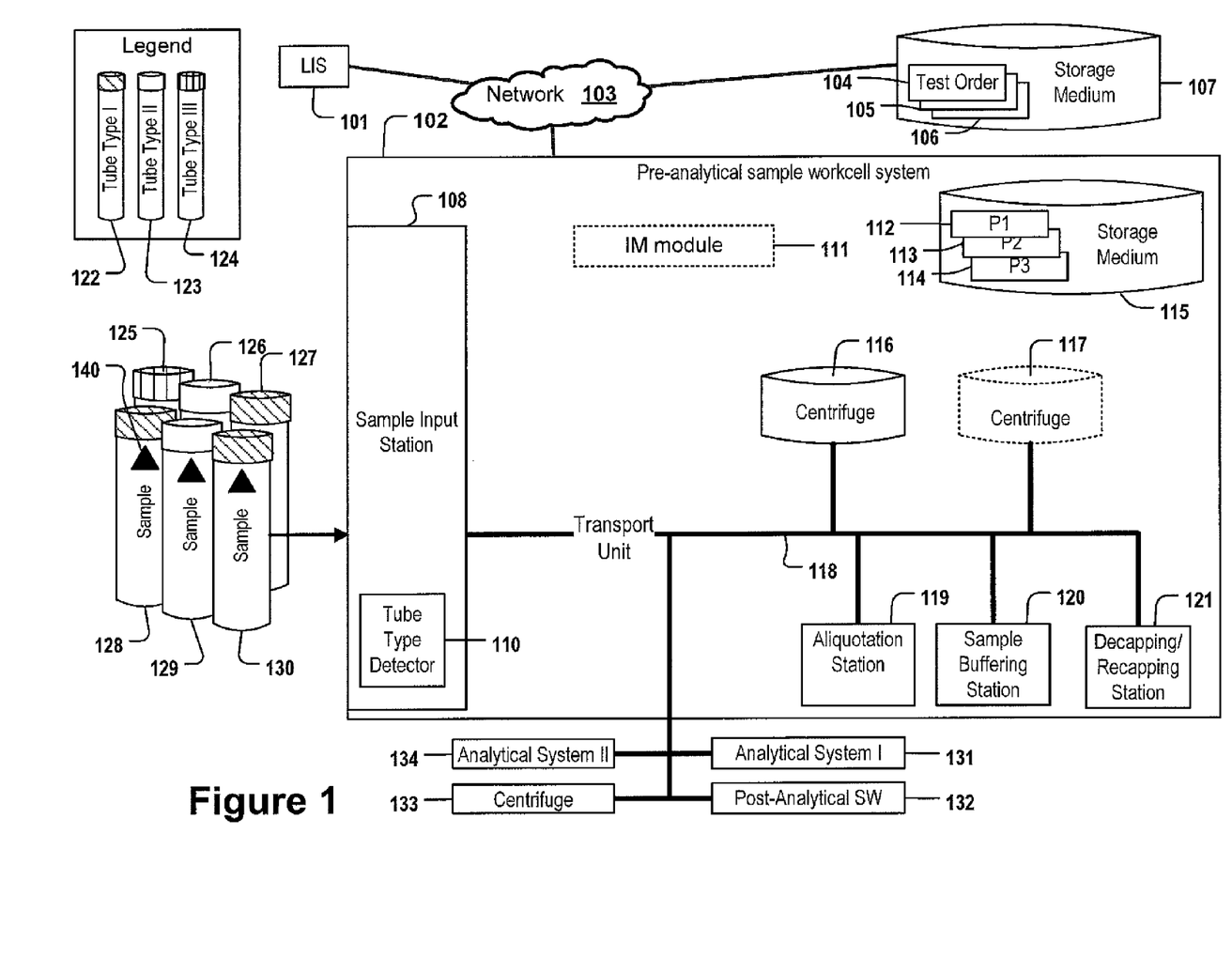
FIG. 1 illustrates a block diagram of an automated sample workcell according to an embodiment of the present disclosure.

Referring initially to FIG. 1, FIG. 1 is a block diagram of a sample workcell 102 according to one embodiment of the present disclosure. The automated sample workcell 102 can comprise a sample input station 108, at least one centrifuge 116, 117, a transport unit 118 in the form of a sample conveyor for automatically transporting biological samples 125-130 from the sample input station 108 to one of the centrifuges 116, 117 or any of the other sample processing units 119-121 such as, for example the aliquotation station 119 or the decapping/recapping station 121. The transport unit may also transport the biological samples to the sample buffering station 120 or unload the biological samples from the buffering station. According to FIG. 1, the transport unit can forward the at least one received biological sample, after having executed one or more pre-analytical processing steps on the sample, to one or more analytical systems 134, 131, and also to a post-analytical sample workcell 132.

Each sample can be labeled with a label being particular for the sample or for a particular patient from which the sample was derived. In addition, a sample may have attached a tube type label for identifying the tube type. Such a tube type label can be used instead of a complex image recognition unit for determining the type of a tube. According to this embodiments, the tube type is not determined by evaluating its color or dimensions but rather by reading the tube type ID from the tube type label. The tube type can be detected by tube type detector 110 which can be, for example, a camera in connection with an image analysis device that can determine the tube type by analyzing for example the color and/or shape of the tube cap or the tube. Tube type detector 110 may likewise be an RFID tag reader, a 2D or 3D code reader.

The workcell 102 depicted in FIG. 1 can further comprise a computer readable storage medium 115 having stored therein computer interpretable instructions 112-114 which can be selected based on a received test order and/or based on the tube type 122-124 of the sample tubes. The set of selected computer implemented instructions can respectively specify the one or more first or second processing steps.

The instrument manager (IM) module 111 is a software-, hardware- or firmware-module which can be, depending on the embodiment, integral part of the sample workcell or of a LIS 101 or of a laboratory middleware being connected to the automated sample workcell 102 via a network 103. The IM module can evaluate a received test order and a detected tube type in order to determine the first or second processing steps to be executed on the at least one biological sample. The IM module can further coordinate and control the one or more lab-devices 116-121, including the transport unit, which can execute the one or more first or second processing steps on the biological sample. According to FIG. 1, the sample tube types 122-124 can be indicated by a particular hachure of the sample caps.

Figure 2:
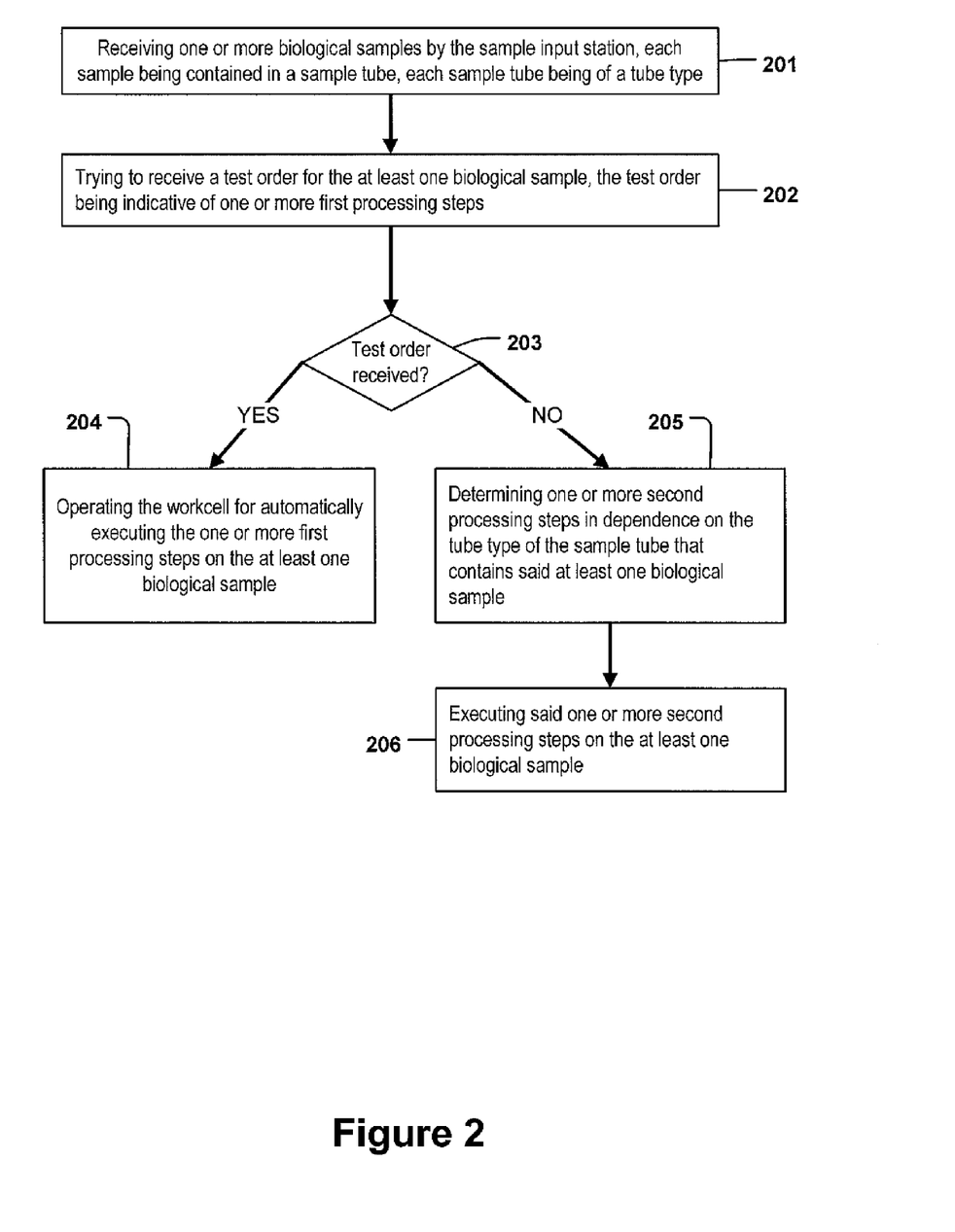
FIG. 2 illustrates a flowchart of a method for operating the automated sample workcell according to an embodiment of the present disclosure.

FIG. 2 depicts a flowchart of a method for operating an automated sample workcell 102. In a first step, the sample input station 108 of the automated sample workcell can receive one or more biological samples 125-130. The sample tubes loaded into the sample workcell may be contained in sample tubes of different types. The samples may be loaded into the sample input station individually or rackwise. Upon having received the at least one biological sample, the automated sample workcell can try 202 to receive a test order for the at least one biological sample. This step may comprise submitting a first request by the IM module to LIS or middleware components. Submitting the first request may also be based on executing a read operation on a data storage medium 107 to which test orders are stored as soon as they have been specified and assigned to a particular biological sample.

In decision step 203, the IM module can determine if the requested test order was received. If the requested test order was received for the at least one biological sample in response to the first request, the sample workcell in step 204 can automatically execute one or more first processing steps on the at least one biological sample. The one or more first processing steps can be determined by evaluating the received test order and determining the one or more first processing steps which can be necessary to prepare the biological sample for an analytical test requested in the test order for the sample.

If a test order was not received, one or more second processing steps can be determined in step 205 based on the tube type of the sample tube which contains the at least one biological sample. In one embodiment, the tube type can be determined by the tube type detector 110 automatically whenever a sample is loaded into the sample workcell. In another embodiment, the tube type can be determined by the detector 110 only in case it was determined in step 203 that no test order was received in response to the first request.

After having determined the one or more second processing steps, the second processing steps can be executed on the at least one biological sample automatically by one or more lab-devices/units of the automated sample workcell.

Figure 3:
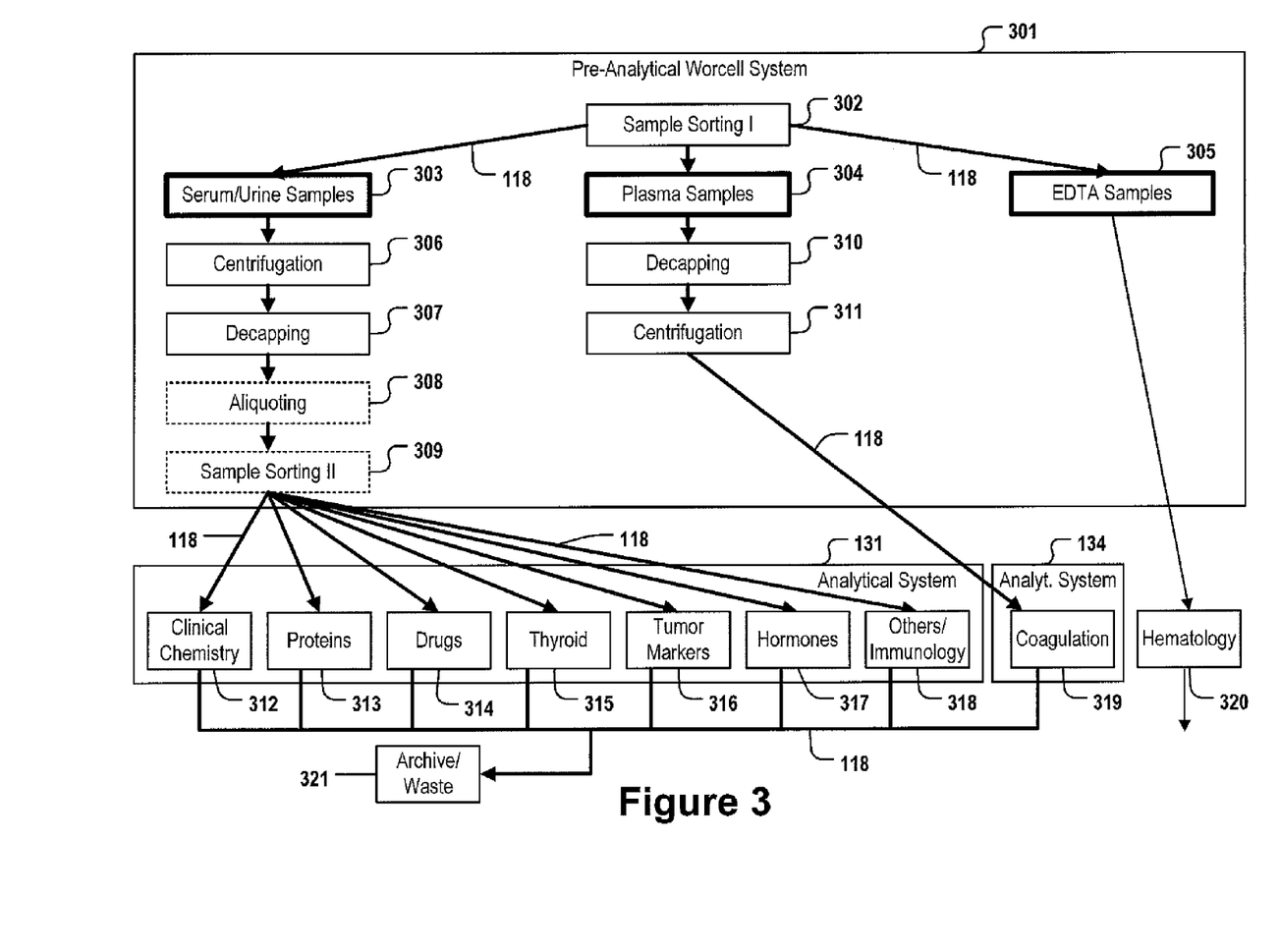
FIG. 3 illustrates the processing of three different types of samples according to an embodiment of the present disclosure.

FIG. 3 depicts the grouping of samples into three different sample groups. The grouping can be test order based if a test order was received for the samples respectively. The grouping can be tube-type based if a test order was not received. In processing step 302, a plurality of received biological samples can be grouped and the groups can be forwarded by transport unit 118 to different lab-devices of the work cell.

For instance, all biological samples contained within a serum/urine sample tube can be processed by the following second processing steps: centrifugation 306 in centrifuge 116 for obtaining serum from whole blood; decapping 307 in the decapping/recapping station 121; aliquotation 308 in aliquotation station 119, and a second sorting step 309 for grouping the one or more samples based on the analytical test 312-318 to be performed on that sample and for automatically transporting all samples to the corresponding analytical system 131. Processing steps 308 and 309 are depicted with dotted borders as the processing steps can only be executed if a test order was received, but not if only the tube type of a sample is known. Steps 306 and 307, however, can be executed based on the sample tube even if a test order was not received.

Correspondingly, the steps 310 and 311 can also be executed on whole blood samples in plasma tubes even if no test order was received for the samples. The plasma samples 304 can be decapped in step 310 in decapping/recapping station 121 and can be centrifuged 311 in centrifuge 117 for obtaining plasma from the whole blood. In a further step, provided a test order was received in response to a first or a second request, the test order requesting for a coagulation test, the samples can be forwarded to analytical system 134 for executing the requested coagulation test 319. In a final step, the analyzed biological samples may be forwarded to an archive for storing the biological samples for further analyses or to a waste unit 321 for disposing the samples.

EDTA samples 305 cannot be centrifuged but rather collectively forwarded by the transport unit 118 to an output buffer. From the output buffer, the EDTA samples can manually, or automatically, be forwarded for executing hematological tests 320.

Figure 4:
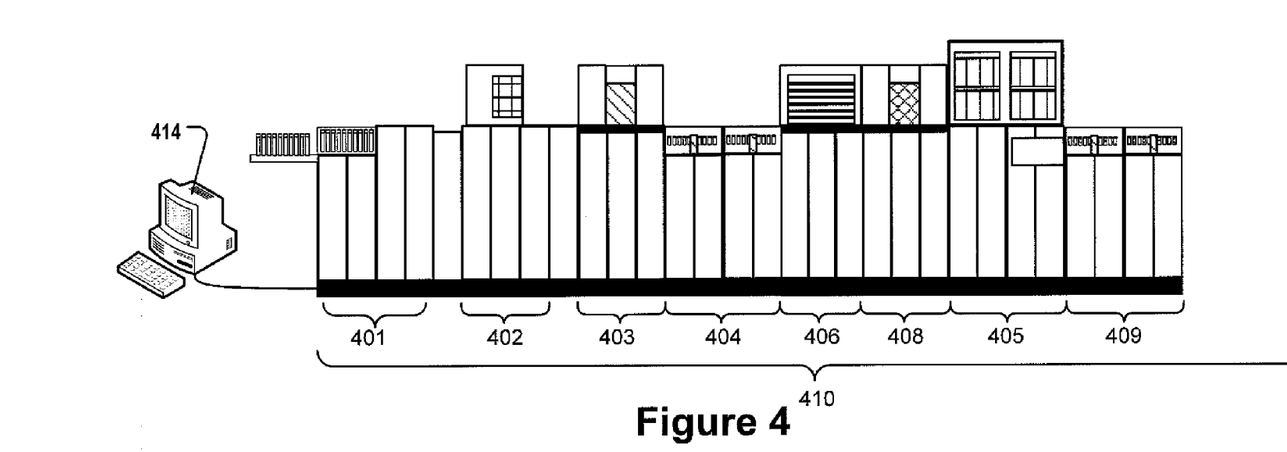
FIG. 4 illustrates a pre-analytical sample workcell according to an embodiment of the present disclosure.

FIG. 4 depicts a pre-analytical automated sample workcell 410 which can comprise a plurality of processing lab-devices or 'units' 401-409. Each unit can be responsible for executing one or more pre-analytical processing steps on one or more biological samples. Each unit can be connected to at least one other unit by a conveyor acting as transport unit. The modular architecture of the pre-analytical automated workcell can be advantageous, because it can be allowed to freely combine the units according to the specific needs of a particular laboratory. The sample workcell 410 can be connected to a computer system 414 directly, or via a network. A user can create and assign test orders to one or more samples which can be processed by the sample workcell via a graphical user interface (GUI) of the computer system 414. The GUI may in addition provide a user with dynamically updated status information indicating the processing steps to be executed and/or having already been executed on a particular sample.

Unit 401 can be a sample input station which can buffer a plurality of biological samples loaded into the input station. It can comprise a bar code reader for identifying a biological sample by reading and evaluating a bar code attached to each biological sample. According to one embodiment, the sample input station can further determine the STAT status of the received samples based on the assigned test orders or based on the input location of the samples (according to another embodiments, the sample input station can comprise different entry points for STAT samples and for ROUTINE samples), thereby allowing for the processing of STAT samples with highest priority. The sample input station can further comprise a tube type detector 108 for determining the type of a tube, e.g. based on image analysis. The tube type detector may be a camera in combination with a software module that can execute image analysis for determining the tube type. According to one embodiment, the image analysis module may also be part of the IM module. A light source can provide sufficient illumination of the samples.

Unit 402 can comprise a centrifuge that can be programmed based on the test order, or, if no test order is available, based on the tube type of the received biological samples. One or more biological samples can be automatically loaded to and unloaded from the centrifuge by the transport unit connecting all units of the automated sample workcell 410 with each other. Unit 403 can be a decapping module that can decap tubes of a plurality of tube types such as, for example, Hemogard, Venosafe, Monovette, Kabe and Kima.

Unit 404 can be an aliquoter module that can aliquot biological samples for a variety of different analyzer systems. Unit 405 can be a sample sorter module that can group a plurality of samples based on their assigned test order and/or based on the tube type the samples are contained in. The sorted sample groups can then be forwarded by the transport unit to different analytical systems and/or post-analytical sample workcells. Unit 406 can comprise a bar code labeler that can label biological samples with computer-readable and/or human readable data. Unit 408 can be a recapping module that can cap and/or recap a plurality of different tube types. Unit 409 can be an output sample buffer that can buffer a plurality of samples which have been processed and which are ready for storage and/or disposal.

Figure 5:
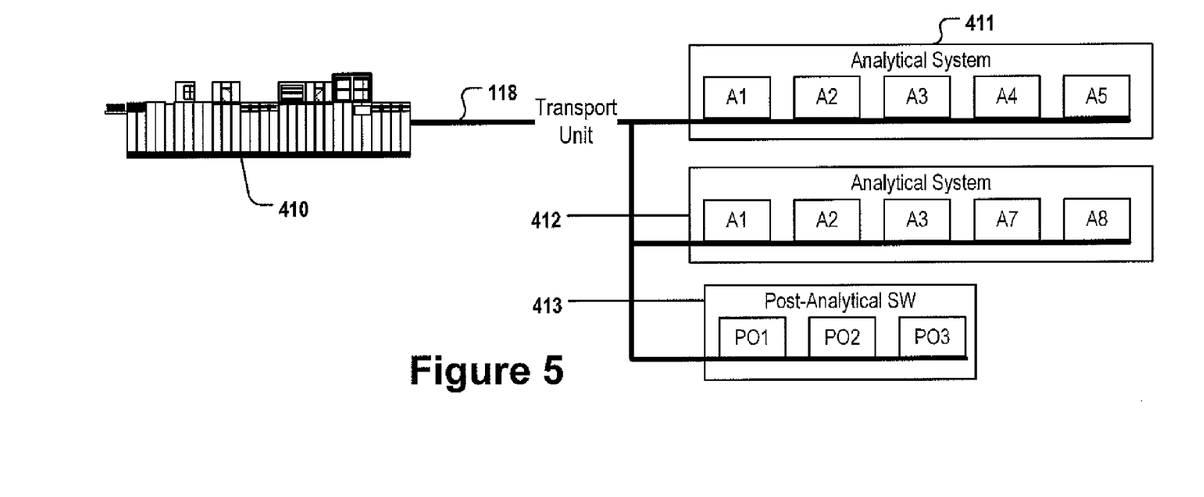
FIG. 5 illustrates the pre-analytical sample workcell in connection with two analytical systems and a post-analytical sample workcell according to an embodiment of the present disclosure.

FIG. 5 depicts a combination of the pre-analytical automated sample workcell 410, two analytical systems 411, 412 and one post-analytical sample workcell 413. The analytical systems can be multi-modular analytical systems comprising a series of analytical units A1-A5 and A1, A2, A3, A7, A8, respectively. Each analytical unit A1-A8 can execute a particular set of analytical tests on one or more biological samples. After having analyzed one or more aliquots of the at least one biological sample in one or more analytical units A1-A8, the sample may be forwarded to the post-analytical sample workcell for long-term storage or disposal. The post-analytical sample workcell 413 can comprise three post-analytical lab-devices PO1-PO3 which can be, for example, a cooled storage unit such as a refrigerator or a freezer, a waste unit and the like. The pre-analytical sample workcell 410, the analytical systems 411, 412 and the post-analytical sample workcell 413 can be connected to each other via transport unit 118, e.g. a conveyor belt.

Figure 6A:
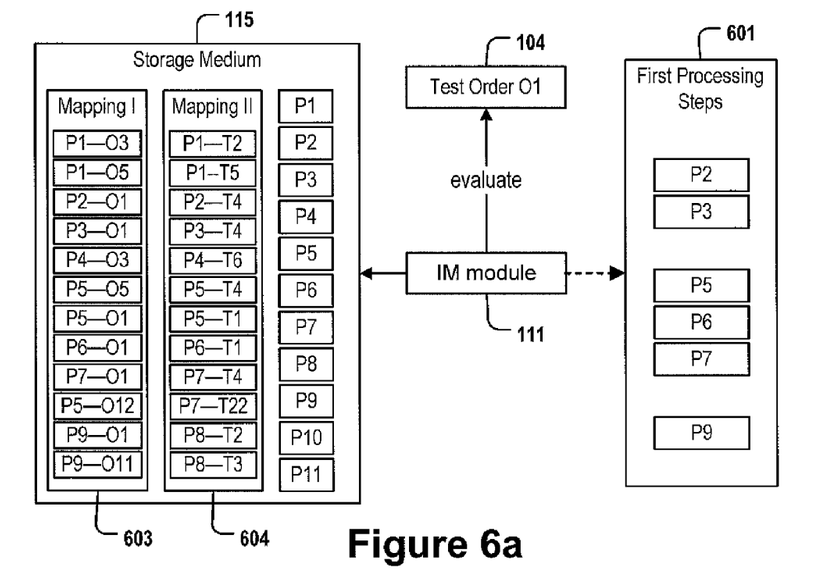
FIG. 6*a* illustrates the selection of computer implemented instructions specifying one or more first processing steps based on a received test order according to an embodiment of the present disclosure.
Figure 6B:
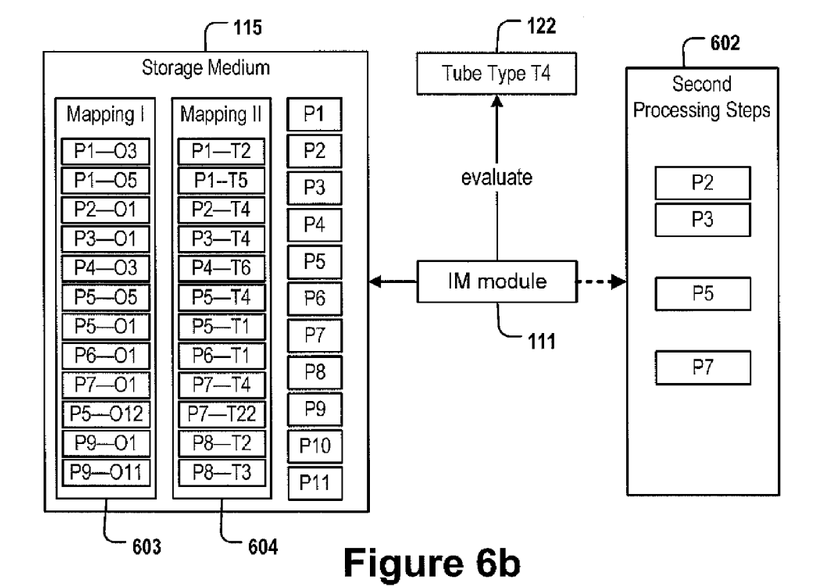
FIG. 6*b* illustrates the selection of computer implemented instructions specifying one or more second processing steps based on the tube type according to an embodiment of the present disclosure.

FIGS. 6a and 6b depict a computer readable storage medium 115 having stored therein a plurality of programs P1-P11. Each program can be a set of computer interpretable instructions specifying a particular processing step which can be executed physically on one or more biological samples by one particular lab-device 401, . . . , 409 of an automated sample workcell 410. The storage medium 115 can further comprise a first mapping 603 which maps each program P1, . . . , P11 to one or more test orders O1, . . . , On. The storage medium can further comprise a second mapping 604 which maps each program P1, . . . , P11 to one or more tube types T1, . . . , Tm. The characters n and m respectively represent integers larger than 1.

If a test order O1 104 was received by the automated sample workcell for a particular biological sample as depicted in FIG. 6a, the IM module can select one or more programs P2, P3, P5-P7, P9 based on the received test order O1, thereby specifying the one or more first processing steps. If the test order O1 104 was not received by the automated sample workcell for a particular biological sample, the IM module can select one or more programs P2, P3, P5, P7 based on the tube type 122 T4 of the biological sample, thereby specifying the one or more second processing steps. The latter case is depicted in FIG. 6b. The IM module can control and monitor the execution of the one or more first or second processing steps by the automated sample workcell.

In the following, two use-case scenarios will be described to elucidate the differences between state-of-the-art sample workcells and embodiments of the present disclosure. Some of the advantages provided by embodiments of the present disclosure can be the avoidance of delays which occur in state-of-the art test-order based sample workcells having received a biological sample to which no test order has been assigned yet.

Two Use-Case Scenarios

Scenario I: State-of-the-Art Sample Workcell a) If a biological sample is loaded into a state-of-the-art test order-based sample workcell and the workcell is operable to receive a test order for the biological sample, the workcell can determine one or more processing steps to be executed on the received biological sample based on the received test order.

b) If a biological sample is loaded into an automated sample workcell and the workcell is not able to receive a test order for the sample, the state-of-the art sample workcell cannot process the sample because no information on how to prepare the sample for one or more analytical tests is available. As a consequence, the samples have to be manually or automatically carried to a buffering station or a storage unit. The samples can be kept in the buffering station or storage unit until a corresponding test order is available. Valuable time can be lost and buffering/storage capacities are occupied. An operator of the workcell may in addition be burdened with the task of deciding what to do with samples not having assigned any test order.

Scenario II: Sample Workcell According to Embodiments of the Invention a) The automated sample workcell receives at least one biological sample by its sample input station and successfully requests or otherwise receives a test order for then sample. If a test order for the biological sample was received, the automated sample workcell can execute first processing steps on the sample as indicated by the test order. For instance, if the received biological sample is a whole blood sample having assigned a test order for executing a glucose level analysis, the automated sample workcell can transfer the sample to a centrifuge, can initiate the centrifugation of the sample in accordance with a centrifugation program appropriate for the indicated analytical test, and can forward the centrifuged biological sample to one or more analytical devices as indicated in the received test order.

b) If the test order for the biological sample was not received, the automated sample workcell can execute one or more second processing steps based on the tube type of the received biological sample. While state-of-the-art test-order based sample workcells are not able to process a biological sample if no test order was received or are merely able to execute some static, predefined processing steps such as forwarding the samples to a buffering station, some embodiments can allow for the execution of one or more complex processing steps on the samples based on the dynamically determined tube type of the sample. Thereby, automated sample workcells according to some embodiments can flexibly process a sample according to its tube type even in case a test order is not available for a sample at that moment. Using the tube type in order to determine at least some processing steps can be advantageous, because information on the tube type is automatically available whenever a biological sample is loaded into a sample workcells even if a test order has not yet been received. For example, if a whole blood sample contained in a serum tube was received by the sample workcell, the sample workcell is able to execute decapping or recapping steps and a centrifugation step for preparing serum from the whole blood. The processing steps having been determined based on the tube type of a sample are herein also referred to as 'second processing steps'. Although some processing steps necessary for preparing the sample for a particular analytical test may not be deducible from the tube type alone, determining one or more second processing steps based on the tube type if a test order is not available guarantees that necessary processing steps can be executed immediately after the receipt of the biological sample by the workcell even if no test order was received.

Pre-Processing Blood Samples for Coagulation Tests

To give a concrete example of an embodiment in practice, the processing of coagulation samples by an automated sample workcell will be described. If a test order for a 'coagulation test' was received for the at least one biological sample of a patient, e.g. in response to a first request, one or more first processing steps are executed on the sample as indicated by the test order. The first processing steps are pre-analytical sample processing steps which prepare the sample for a succeeding coagulation analysis. The first processing steps comprise: programming the centrifuge for executing a centrifugation step of 3000 g for 10 minutes; executing the centrifugation step on the sample; decapping the sample by the decapping station; and aliquoting the sample by the aliquotation station. The sample aliquots may then automatically be transported to an appropriate analytical system or to an output buffer from which the sample can be manually transferred to an analytical system for executing the coagulation test.

If the test order was not received in response to the first request, the workcell does not have to suspend processing the sample until the test order is received as is the case in prior art systems. Rather, a tube type detection unit within the input station of the workcell can dynamically determine the tube type. Then, one or more second processing steps are determined based on the tube type. If the tube type was recognized as coagulation sample tube (type VI for coagulation tests according to Table 1), the centrifugation program is specified accordingly and the sample is centrifuged according to the program also in the absence of a test order. The second processing steps in this example are pre-analytical sample processing steps which prepare the sample for a succeeding coagulation analysis as far as possible based on the information provided by the tube type. The second processing steps comprise: programming the centrifuge for executing a centrifugation step of 3000 g for 10 minutes; executing the centrifugation step on the sample; and the sample is then forwarded to a buffering station. In the buffering station, the sample is stored until a test order for the coagulation sample is available which is used to determine and execute outstanding processing steps, e.g. the aliquotation steps.

If the test order was meanwhile received, e.g. in response to a second request and while executing the centrifugation step, the step of transporting the sample to the buffering station can be omitted and outstanding processing steps indicated by the meanwhile received test order which have not yet been carried out can be executed. The processing steps are, in this example: forwarding the sample to an aliquotation station for aliquoting the sample; automatically transporting the sample aliquots to an appropriate analytical system or to an output buffer from which the sample can be manually transferred to an analytical system for executing the coagulation test.

Pre-Processing Blood Samples for Clinical Analysis

According to this embodiment, the workcell can automatically pre-process whole blood samples being contained in serum tubes for a variety of different clinical tests. The samples need to be centrifuged with a centrifugal force of 2000 g and a centrifugation time of 5 minutes for preparing serum from the whole blood (the same centrifugation parameters are also used for preparing plasma-samples). If the automated sample workcell can receive the test order for the blood sample, e.g. a request for executing a test for determining the glucose level, the sample workcells executes one or more first processing steps. Those first processing steps comprise centrifuging the sample with a centrifugal force of 2000 g for 5 minutes and executing additional pre-processing steps necessary for preparing the sample for determining its glucose concentration. If the test order was not received, at least the centrifugation step and e.g. some decapping and/or recapping steps are automatically executed based on the sample tube type (serum sample, tube types I and II according to Table 1).

Pre-Processing Blood Samples for Hematological Tests

According this embodiment, the workcell can automatically pre-process EDTA-blood samples collected in type III sample tubes. Blood collected in the sample tubes may be used to examine the blood cells, e.g. their shape and number per volume unit. For this type of analysis, also referred to as hematological test, a centrifugation could render the execution of the analysis impossible. A centrifugation of the samples must therefore be prohibited. The first or second processing steps to be executed on this type of samples therefore may comprise various decapping- and/or recapping-steps, but not any centrifugation step.

Pre-Processing STAT Samples

The sample workcell may in addition automatically pre-process STAT samples with a higher priority than routine samples. If a test order was received for the at least one received biological sample, its STAT-status, i.e. its categorization as STAT sample or as ROUTINE sample, is determined based on the received test order. In addition, one or more first processing steps are executed on the sample as indicated by the test order. If the test order was not received, the STAT status of the biological sample is determined based on the input location of the sample input station having received the at least one biological sample. If the sample was categorized as STAT sample, the sample is processed with higher priority than the routine samples. This can be advantageous, because if STAT samples are received by the sample workcell, the STAT samples can be identified as STAT samples and can be immediately processed with highest priority based on the input location having received the samples even if a test order was not yet received for the sample.

Operating a sample workcell according to these embodiment can be advantageous, because at least some 'second' processing steps are executed by the automated sample workcell even if no test order was received for the sample by the automated sample workcell.

Depending on the embodiment, the test order for the at least one biological sample can be received based on a push- or a pull approach. For example, a test order received via the push approach may be submitted to the automated sample workcell from the LIS or another piece of laboratory software as soon as the test order is specified for a particular biological sample. In the following, the expression 'receiving a test order' encompasses any push- or pull-based approach for receiving a test order for a biological sample.

According to some pull-approach based embodiments, the automated sample workcell tries to receive a test order for the at least one biological sample by executing a first request. Depending on the embodiment, executing the first request may comprise submitting an electronic request for a test order via a network to the middleware or the LIS, e.g. a Web-service request, a remote procedure call or the like. The first request may also comprise executing a read operation on a computer readable storage medium in order to determine whether a test order for the received biological sample has been stored to the storage medium.

The test order can be indicative of one or more first processing steps. The expression 'being indicative' implies that the test order itself may comprise instructions, e.g. computer interpretable instructions for executing the one or more first processing steps on the biological sample. In addition or alternatively, the test order may comprise one or more identifiers of one or more analytical tests and/or pre-analytical and/or post-analytical processing steps to be executed on a sample. A test order may also be indicative of a complex sample processing workflow covering pre-analytical, analytical and/or post-analytical sample processing steps. Detailed computer interpretable instructions for triggering one or more lab-devices of the automated sample workcell to execute the physical processing steps on the biological sample can be a part of the test order itself or can be stored elsewhere in association with one or more identifiers contained in the test order.

According to some embodiments, the automated sample workcell can comprise lab-devices for executing one or more processing steps selected in any combination from the group comprising pre-analytical processing steps, analytical processing steps and post-analytical processing steps.

According to some embodiments, the automated sample workcell can be a pre-analytical sample workcell and each test order specifies at least one analytical test to be performed on the at least one biological sample. The one or more first processing steps thereby may be indicated, for example, by the at least one analytical test.

According to some embodiments, requesting a test order for a particular biological sample can comprise reading a label of a biological sample in order to determine a sample identifier being encoded by the label and to submit a request for a test order for the sample, wherein the request comprises the sample identifier.

According to some embodiments, the automated sample workcell can comprise one or more lab-devices.

According to some embodiments, selecting one or more second programs from the plurality of first programs based on the received test order or based on a tube type can be implemented by providing a computer readable storage medium having stored therein a plurality of first programs, whereby one or more first programs can be respectively stored in association with one or more test order identifiers. In addition, one or more first programs can be respectively stored in association with one or more tube type identifiers. Each first program can thereby comprise computer interpretable instructions specifying how to physically conduct a processing step on a sample, e.g. how to transport a sample to a particular centrifuge or how to execute a centrifugation step on a sample. This can be advantageous, because this embodiment allows the flexibility to assign one or more processing steps to a particular sample tube identifier and/or to a particular test order by means of a mapping. The mapping can be implemented e.g. by means of an association table of a relational database, whereby each program is mapped to one or more identifiers of a test order and/or to one or more identifiers of a tube type. As a consequence, an operator of the automated sample workcell can change workflow definitions simply by editing a table of a relational database. This embodiment can also allow the flexibility to program highly complex workflows which can be executed based on a dynamically determined sample type in case a test order was not received.

Executing one or more first processing if a test order was received for the sample may comprise, according to some embodiments, receiving an identifier of an analytical test or of a single sample processing step, whereby the identifier is contained in the received test order. Then, one or more computer interpretable instructions having been stored in association with the received test order identifier are read from a computer-readable medium. The one or more received computer implemented instructions specify one or more first processing steps to be executed by the sample workcell on the biological samples.

Executing one or more second processing based on the tube type may comprise, according to embodiments, determining the sample tube type, evaluating the sample tube type for obtaining a tube type identifier and reading computer interpretable instructions from a data storage medium, whereby the instructions were stored to the storage medium in association with one or more tube type identifiers and whereby only those instructions are read which have assigned the obtained tube type identifier.

According to embodiments, the automated sample workcell can try to receive a test order for the at least one biological sample by executing a first request. According to some embodiments, the execution of the first request can be triggered by the receipt of the at least one biological sample by the workcell or one of its components, e.g. its sample input station. For example, the sample input station notifies an IM (instrument manager) module that a sample having assigned a particular sample-ID was received, and the IM module requests in a first request for a test order for the sample.

According to further embodiments, at least one second request can be automatically executed for receiving the test order. The at least one second request can be executed at a moment being selected from the group comprising: after a predefined time period after having executed the first request such as, for example, a second request may be submitted 5 min. after having submitted the first request; after having executed the first request and while executing one of the one or more second processing steps such as, for example, the automated sample workcell may execute a centrifugation step as part of the second processing steps based on the tube type. While executing the centrifugation, the automated sample workcell may submit one or more second request for receiving a test order for the centrifuged sample. This can be advantageous, because not all sample processing steps which are necessary in order to prepare the biological sample for a particular analysis according to a test order can be determined as 'second processing steps' based on the tube type. In order to determine also those 'test order-specific' processing steps, it can be beneficial to start executing the second processing steps immediately and trying in parallel to receive an indication of all outstanding processing steps by submitting one or more second requests. After having executed one of the one or more second processing steps, whereby the one or more second processing steps according to some embodiments comprise transporting the at least one biological sample to a buffering station after all other second processing steps have been completed. This feature of transporting the at least one biological sample to a buffering station after all other second processing steps have been executed can be advantageous, because this step guarantees that a sample does not block the processing of other samples and is stored under appropriate storing conditions if a test order is still not available after having finished executing the one or more second processing steps. For example, a temperature sensitive sample can be transferred to a cooled buffering station, thereby guaranteeing that the sample can still be used for a chemical analysis later on as soon as the test order is received by the sample workcell.

According to some embodiments, the one or more second processing steps can comprise one final step of transferring the at least one biological sample to a storage unit after having executed all other second processing steps. According to some of the embodiments, the final transportation step is not executed if, while executing one of the second processing steps, the test order was received in response to one of the second requests. This can be advantageous because it avoids executing unnecessary transportation steps (to and from a sample storage unit).

According to embodiments, the one or more second requests are only submitted if no test order was received in response to the first request.

According to some embodiments, the automated sample workcell can comprise at least one centrifuge. If the test order was received, the executed one or more first processing steps can comprise at least one centrifugation step. The centrifugation step can be executed by the at least one centrifuge as indicated by the test order. If the test order was not received, the executed one or more second processing steps can also comprise the at least one centrifugation step. In this case, the centrifugation step can be determined based on the determined tube type of the sample. This can be advantageous because centrifugation steps can take a considerable amount of time and are often the time limiting step of a workflow. Therefore, executing a centrifugation step based on the tube type if a test order is not available can help avoid bottlenecks. In many cases, delays resulting from a delayed assignment of a test order to a sample can be completely avoided because the centrifugation step can be started based on the tube type if the test order cannot be received at the moment when the sample is received by the sample input station of the workcell. As a centrifugation step may take 5-20 min., there is a good chance for receiving the test order in response to one of the one or more second requests during or after the execution of the centrifugation step.

According to further embodiments, the automated sample workcell can comprise at least one aliquotation station. If the test order was received, the one or more executed first processing steps can comprise at least one aliquotation step to be executed on the at least one biological sample by the at least one aliquotation station. If the test order was not received, the one or more executed second processing steps do not comprise the at least one aliquotation step. This can be advantageous because the step of aliquoting a biological sample typically depends on the analytical test to be executed and can therefore often not be executed based on information on the tube type alone. Executing the step of aliquoting a sample only if the test order was received can be advantageous, as it can ensure that only those processing steps are executed whose necessity can safely be deduced from the tube type.

According to further embodiments, the automated sample workcell can comprise at least one decapping and/or recapping station. If the test order was received, the one or more executed first processing steps can comprise at least one decapping and/or recapping step to be executed on the at least one biological sample by the at least one decapping and/or recapping station. If the test order was not received, the one or more executed second processing steps can comprise the at least one decapping and/or recapping step. This can be advantageous because capping, decapping and recapping a sample may be a necessary pre-analytical procedure in a variety of different workflow settings. The first as well as the second processing steps may comprise one or more decapping and/or recapping steps in the order needed in a particular state within the workflow.

If the test order was not received and the sample is processed based on the sample tube, the sequence of workcell lab-devices used for executing one of the one or more second processing steps may differ from the sequence and/or type of workcell lab-devices used for executing the one or more first processing steps. Some processing steps may require the sample to be capped, others may require it to be decapped. According to some embodiments, the first processing steps as well as the one or more second processing steps can comprise one or more capping and/or decapping processing steps. The capping and/or decapping processing steps can be arranged within the first and/or second processing steps as needed by the workcell lab-devices executing the first/or second processing steps.

According to further embodiments, the one or more second processing steps can be a subset of the one or more first processing steps. If the test order was not received at the moment when the sample workcell receives the one or more biological samples, e.g., if no test order is received in response to the first request, the one or more second processing steps can be executed. After having executed the one or more second processing steps, further steps can be executed by the automated sample workcell which can comprise: receiving, after having finished executing the one or more second processing steps, the test order (the test order may, for example, be received in response to a second processing step); determining one or more outstanding processing steps, the one or more outstanding processing steps comprising all first processing steps not being contained in the one or more second processing steps having been executed already; and executing the one or more outstanding processing steps by the automated sample workcell after having executed the one or more second processing steps. In other words, after having executed the second processing steps and after having received the test order at a later moment in time, e.g. in response to a second request, all those processing steps indicated by the test order are executed which have not yet been executed already as second processing steps based on the tube type. This can be advantageous because this can ensure that by executing the one or more outstanding processing steps, finally all processing steps can be executed which are necessary to prepare the sample for a particular analytical test requested in the test order of the sample.

For instance, the sample workcell may receive a whole blood sample within a serum tube and submit a first request for a test order of the tube in response to the receipt of the sample. However, no test order is received in response to the first request. The workcell may determine that the received biological sample is contained in a serum tube and may execute one or more second processing steps based on the dynamically determined tube type. The second processing steps can comprise a centrifugation step for preparing serum from the sample. As the information that can be deduced from the tube type is not specific enough to allow executing an aliquotation step, the sample workcell is not able to aliquot the sample for a particular analytical test. Therefore, the workcell may submit one or more second requests and may forward the sample after having finished the second processing steps to a storage unit if no test order was received in response to the second requests. If, however, the test order of the sample was received during or after the execution of the one or more second processing steps, the one or more outstanding processing steps can be determined automatically as an intersection of all the first processing steps indicated by the test order and all second processing steps having already been executed by the workcell. After having determined one or more outstanding processing steps, the one or more outstanding processing steps are executed by the sample workcell, thereby guaranteeing that all first processing steps are actually executed on the at least one biological sample as they would have been if the test order would have been received right away in response to the first request. According to embodiments, the step of aliquoting the sample for a particular analytical test can be executed either as one of the one or more first processing steps or as one of the one or more outstanding processing steps.

According to further embodiments, the at least one second request can be repeatedly and automatically executed. This can be advantageous because a second request is continuously, e.g. after predefined time intervals, executed during and/or after the workcell executes the one or more second processing steps. This can guarantee that the test order is received as soon as possible, thereby avoiding that a sample for which a test order can meanwhile be received is unnecessarily transferred to a buffering unit. If no test order was received when all second processing steps are executed, the sample may be transported to the sample buffering station. According to some embodiments, the one or more second requests can be repeatedly executed even after having transferred the sample to the buffering station. As soon as the test order was received in response to a second request, the sample is unloaded from the buffering station for executing one or more outstanding processing steps on the sample.

According to embodiments, the sample workcell can comprise an instrument manger (IM) module. The module can be a hardware-, firmware- or software module or any combination thereof. The IM module can act as a control instance which controls and monitors the processing steps executed by lab-devices of the sample workcell. The IM module can submit the first and second requests and can receive the test orders in response to any of the first or second requests. The IM module can receive the tube type having been determined by the tube type detector. According to embodiments, the IM module can access a computer-readable storage medium having stored therein instructions which specify the physical processing steps executed by the workcell lab-devices. According to embodiments, the IM module can be an integral part of the sample workcell. According to other embodiments, the IM module can be a software module being part of the middleware or LIS of a laboratory, the middleware or LIS being connected to the workcell via a network, e.g. an intranet.

According to some embodiments, the test order is not received when the one or more samples are loaded into the sample workcell. The automated sample workcell can receive the test order while the workcell is executing the one or more second processing steps on the sample or has finished executing the one or more second processing steps. For example, the test order, e.g. in response to one of the second requests, the sample workcells or one of its components, e.g. the IM module, compares the second processing steps with the first processing steps indicated by the meanwhile received test order. If the comparison returns as result that one or more of the executed second processing steps are not indicated by the test order, the workcell can automatically detects the sample as a wrongly processed sample. The workcell can submit an alert message which is indicative of the wrongly processed sample. In addition or as an alternative to submitting the alert, the sample can be transported to a buffer unit for storing or discarding erroneously processed biological samples. For example, the IM module of the workcell may automatically detect a wrongly processed sample and submit an alert message via a network to an LIS or other software component of the lab and may be displayed on a GUI. These features can be advantageous as they can detect and sort out samples whose tube type was not recognized correctly and which may therefore have been processed erroneously. Such samples may not be usable for an analytical test any longer and sorting them out helps to guarantee the accuracy of analytical test results obtained on samples pre-processed by the sample workcell.

According to further embodiments, the sample workcell can determine the tube type of the at least one biological sample. Executing the one or more second processing steps can comprise retrieving a centrifugation program for the determined tube type and executing a centrifugation step according to a centrifugation program. The centrifugation program could be stored e.g. to a computer readable non-volatile storage medium, e.g. an electromagnetic disk, a flash drive, an optical drive or the like, and can be read by the IM module for specifying the centrifugation program of at least one centrifuge and for centrifuging the sample according to the centrifugation program. Depending on the embodiment, the computer readable storage medium may be an integral part of the automated sample workcell, of the centrifuge or of another storage medium being accessible via the middleware or the IM module. Depending on the embodiment, the centrifuge can be an integral part, e.g. a modular unit, of the automated sample workcell, or can be an independent laboratory device connected to the automated sample workcell by an automated transport unit, i.e. a conveyor and/or a robotic arm.

According to further embodiments, determining the tube type can only be executed if the test order was not received. This can be advantageous because determining the tube type, e.g. by means of a camera or other image capturing devices, can be omitted, thereby saving time.

According to other embodiments, the tube type can be determined automatically by a lab-device of the automated sample workcell, e.g. by an image detection device being part of the input station. Depending on the embodiment, the determination of the tube type can be based on an analysis of one or more of the following features being selected from the group comprising: the color of the tube, the color of the tube cap, the dimensions of the tube (i.e. length and/or diameter and/or shape property), the dimensions of the tube cap (length and/or diameter and/or shape property), or a tube type label being indicative of the tube type, e.g. a 2D or 3D code, e.g. a barcode or a matrix code. A shape property can be, for example, depressions or elevations of the surface.

According to further embodiments, a plurality of biological samples can be received and grouped based on respectively received test orders or tube types: if a test order was received for each biological sample belonging to the plurality of received biological samples, the biological samples are grouped according to their respectively received test orders, each sample group sharing the same respectively received test order, before executing the one or more first processing steps. If a test order was not received for each biological sample belonging to the plurality of biological samples, the biological samples of the plurality of biological samples are grouped according to the tube type of each respective biological sample, the samples of each sample group being contained in tubes of the same respective tube type, before executing the one or more second processing steps. This can be advantageous because grouping the samples according to the received test order or the tube type allows to distribute the sample groups to different workcell devices and to process each sample group based on the collectively shared test order. For example, a centrifugation step may be executed on a plurality of samples sharing the same test order in one single step. Accordingly, if the test order was not received, grouping and processing the samples according to a shared sample type can be advantageous because it allows executing a particular second processing step in parallel on a multitude of samples, thereby speeding up the whole sample processing workflow.

According to embodiments, the execution of the first request can be triggered by the receipt of the at least one biological sample. According to further embodiments, the automated sample workcell can be coupled to a data source, the data source having stored a first and a second mapping, the first mapping assigning programs to test orders, the second mapping assigning programs to tube types.

According to still further embodiments, the automated sample workcell can further comprises a light source for illuminating the one or more samples and the tube type detector comprises a digital camera for capturing at least one image of the one or more samples.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure. Although the principles of the present disclosure have been described in the context of blood sample analysis, the embodiments are merely illustrative of the principles and applications of the present disclosure. It is therefore to be understood that numerous modification may be made regarding the type of biological sample to be processed (urine, saliva, cerebral spinal liquor etc), regarding the processing steps to be executed by a lab-device of the automated sample workcell and regarding the test orders and tube types evaluated for determining the first and second processing steps.

TABLE 1

| Tube Types | | | |
|---|---|---|---|
| Tube type | Added substances | Sample type | Possible analyses (indicated in test order) |
| I | contains a clot activator Clot activator accelerates clotting. | serum sample | clinical chemistry on serum (determining glucose/ion/protein level etc.); immunology; routine blood donor screening; diagnostic testing for infectious diseases |

TABLE 1-continued

Tube Types

| Tube type | Added substances | Sample type | Possible analyses (indicated in test order) |
|---|---|---|---|
| II | Contains a clot activator and gel Gel density between density of blood serum and of the blood cells. Gel assists in separating serum and blood cells after centrifugation. Gel prevents substance exchange between blood cell and serum. | serum sample | clinical chemistry on serum (determining glucose/ion/protein level etc.); immunology; routine blood donor screening; diagnostic testing for infectious diseases |
| III | Contains anticoagulant EDTA K2-EDTA does not distort blood cells and is therefore the preferred anti-coagulans for hematological analyses. | hemato-logical samples (whole blood) | clinical hematology examinations of blood cells; routine blood donor screenings; |
| IV | Contains anticoagulants: Heparin, Lithium, Heparin Sodium and gel Gel density is between density of blood plasma and of the blood cells. Gel assists in separating plasma and blood cells after centrifugation. Gel prevents substance exchange between blood cell and plasma. | plasma sample | clinical chemistry on plasma (determining glucose/ion/protein level etc.); immunology; routine blood donor screening; diagnostic testing for infectious diseases; some items of hemorrheology |
| V | Contains thrombin, a rapid clot activator | STAT serum sample | rapid STAT serum analysis |
| VI | Contains anticoagulants citrate Citrate binds the calcium of the blood sample. | citrate-plasma sample | Coagulation analyses: adding calcium allows blood to clot again; determination of e.g. the clotting time; platelet function assays; |
| VII | Urine tubes | urine sample | Chemical analysis on urine samples |

We claim:

1. An automated sample workcell for processing one or more biological samples, the automated sample workcell comprising:
   a sample input station for receiving the one or more biological samples, wherein each biological sample of the one or more biological samples is contained in a sample tube and each sample tube has a tube type;
   an instrument manager (IM) module for receiving test orders for the one or more biological samples and for determining whether a test order was received for the one or more biological samples; and
   a tube type detector for determining the tube type of the sample tube containing the biological samples,
   wherein if the test order was received for the one or more biological samples by the instrument manager, the test order specifies one or more first processing steps for the at least one of the biological samples for which a test order was received by the instrument manager and the automated sample workcell automatically executes the one or more first processing steps on the at least one of the biological samples for which a test order was received, and wherein if the test order was not received for the one or more biological samples by the instrument manager, the automated sample workcell automatically determines one or more second processing steps for the at least one of the biological samples for which a test order was not received based on the tube type of the sample tube that contains the at least one of the biological samples detected by the tube type detector and executes the one or more second processing steps on the at least one of the biological samples for which the test order was not received without delay until the test order is received.

2. The automated sample workcell according to claim 1, further comprising:
   one or more lab devices.

3. The automated sample workcell according to claim 2, wherein the one or more lab devices include: at least one centrifuge, at least one aliquotation station, at least one decapping and/or recapping station, a buffering station, a storage unit, or combinations thereof.

4. The automated sample workcell according to claim 2, further comprising:
   a transport unit for transporting at least one received biological sample from the sample input station to the one or more lab devices.

5. The automated sample workcell according to claim 4, wherein the transport unit is a sample conveyor.

6. The automated sample workcell according to claim 4, wherein the IM module automatically requests in a first request or in the first and at least one second request the test order for the at least one biological sample, wherein if the test order of the at least one biological sample was not received in response to the first or the at least one second request, the transport unit transports the at least one biological sample to a buffering station, and wherein if the test order of the at least one biological sample was received in response to the at least one second request, the transport unit is operable to unload the at least one biological sample from the buffering station and to transport the at least one biological sample to at least one lab device for automatically executing one or more outstanding processing steps on the at least one biological sample, the one or more outstanding processing steps being processing steps which belong to the one or more first processing steps but which have not been executed as second processing steps when the test order is received in response to the at least one second request.

7. The automated sample workcell according to claim 1, wherein at least one of the one or more second processing steps is centrifugation of the at least one of the biological samples for which the test order was not received based on the tube type of the sample tube.

8. The automated sample workcell according to claim 1, further comprising:
   a sample sorter for grouping the one or more biological samples based on whether a test order was received or on tube type.

9. The automated sample workcell according to claim 1, wherein the tube type detector automatically determines tube type for every biological samples received by the sample input station.

10. The automated sample workcell according to claim 1, wherein the tube type detector determines tube type for sample tubes containing the one or more biological samples for which a test order was not received.

11. The automated sample workcell according to claim 1, wherein the tube type detector is a camera in connection with an image analysis device.

12. The automated sample workcell according to claim 1, wherein the tube type detector is a RFID tag reader.

13. The automated sample workcell according to claim 1, wherein the tube type detector is a 2D or 3D code reader.

14. The automated sample workcell according to claim 1, wherein the tube type is determined by one or more of the following: color of the sample tube, color of a tube cap associated with the sample tube, dimensions of the sample tube, dimensions of a tube cap associated with the sample tube, or a tube type label indicative of the tube type.

15. The automated sample workcell according to claim 14, wherein the tube type label is a RFID tag.

16. The automated sample workcell according to claim 14, wherein the tube type label is a 2D or 3D code tag.

17. The automated sample workcell according to claim 1, wherein the tube type determines a centrifugation program for the one or more biological samples for which the test orders were not received.

18. The automated sample workcell according to claim 1, further comprising:
   a buffering station for receiving the one or more biological samples for which test orders was not received after the second processing steps have been completed.

19. The automated sample workcell according to claim 18, wherein the buffering station is a cooling buffering station.

20. The automated sample workcell according to claim 1, further comprising:
   a storage unit for receiving the one or more biological samples for which test orders were not received after the second processing steps have been completed.

* * * * *